United States Patent
Evans et al.

(10) Patent No.: US 6,266,675 B1
(45) Date of Patent: Jul. 24, 2001

(54) SYSTEM AND METHOD FOR USING A RELATIONAL DATABASE TO ENABLE THE DYNAMIC CONFIGURATION OF AN APPLICATION PROGRAM

(75) Inventors: Arnold Kerry Evans, Kent; John Martin Peters, Seattle; Dwight John Barker, Issaquah; William Keith Weinberger, Redmond; William Goodell Barnum, Seattle; Jennifer Chu-hu, Redmond; David E. West, Anacortes; Joseph Rommel Cordero, Seattle; Mary J. Ledbury, New Castle, all of WA (US)

(73) Assignee: PhyCom Corporation, Bellvue, WA (US)

( * ) Notice: Subject to any disclaimer, the term of this patent is extended or adjusted under 35 U.S.C. 154(b) by 0 days.

(21) Appl. No.: 08/946,282

(22) Filed: Oct. 7, 1997

(Under 37 CFR 1.47)

(51) Int. Cl.[7] ............... G06F 19/00; G06F 17/30
(52) U.S. Cl. ............... 707/104; 707/3; 705/3
(58) Field of Search ............... 707/3, 4, 5, 6, 707/2, 100, 102, 200, 104; 705/3

(56) References Cited

U.S. PATENT DOCUMENTS

| 5,369,778 | * | 11/1994 | San Soucie et al. | 707/103 |
|---|---|---|---|---|
| 5,432,931 | * | 7/1995 | Woess et al. | 395/650 |
| 5,434,971 | * | 7/1995 | Lysakowski, Jr. | 395/200 |
| 5,446,575 | * | 8/1995 | Lysakowski, Jr. | 395/200.01 |
| 5,566,330 | * | 10/1996 | Sheffield | 707/4 |
| 5,583,758 | | 12/1996 | McIlroy et al. | 395/202 |
| 5,621,884 | * | 4/1997 | Beshears et al. | 395/182.08 |
| 5,727,158 | * | 3/1998 | Bouziane et al. | 395/200.55 |
| 5,784,635 | * | 7/1998 | McCallum | 395/800.32 |
| 5,802,511 | * | 9/1998 | Kouchi et al. | 707/2 |
| 5,809,266 | * | 9/1998 | Touma et al. | 395/340 |
| 5,900,870 | * | 5/1999 | Malone et al. | 345/333 |
| 5,950,190 | * | 9/1999 | Yeager et al. | 707/3 |

\* cited by examiner

Primary Examiner—Paul V. Kulik
(74) Attorney, Agent, or Firm—Squire, Sanders & Dempsey L.L.P.

(57) ABSTRACT

A computer-based system for using a relational database to dynamically configure an application program easily comprises a relational database including first table means containing first data, second table means containing configuration data, and an engine coupled to the relational database for using the configuration data to configure manipulation of the first data. The engine uses the configuration data to configure the appearance of the user interface, to configure the fields being displayed, to configure the expected type of information to be received, to configure the privileges of the user, to configure the column headers, etc.

22 Claims, 20 Drawing Sheets

FIG. 6A

Activity Template 600

| templateName (605) | templateVersion (610) | description (615) | category (620) | calendarFlag (625) | checkOffFlag (630) | cost (635) |
|---|---|---|---|---|---|---|
| Medication | 1 | Medication Profile | CarePlan | N | Y | 0 |
| Disposition | 1 | Case Disposition | System | N | N | 0 |

Row 1, Row 2

FIG. 6C

Field Description 660

| FieldName (662) | abbrLabel (664) | shortLabel (666) | LongLabel (668) | locationType (670) | locationName (672) | realName (674) |
|---|---|---|---|---|---|---|
| MedDose | Dose | Dosage | Medication Dosage | SQL | Medication | dose |
| MedFrequency | Freq | Frequency | Med Frequency | SQL | Medication | frequency |
| Medical | Med | Medical | Medical | SQL | ProgNote | medical |
| MedPrec | PreCert | PreCert | PreCertification | SQL | Medication | medprec |
| MedPrecdec | Decision | Decision | Decision | SQL | Medication | medprecdec |
| MedPresmd | Presc By | Prescribed By | Prescribed By | SQL | Medication | medpresmd |
| MedProv | Prov | Med Prov | Medical Provider | SQL | ApplGriev | medprov |
| MedRoute | Rt | Route | Medication Route | SQL | Medication | route |
| MedSource | Prv | Source | Med Source | SQL | Medication | source |
| MedType | Type | Med Type | Medication Type | SQL | Medication | type |
| MedUnits | Units | Units | Medication Units | SQL | Medication | units |

Row 1–11

FIG. 6B

Activity Template Fields 640

| | templateName 642 | templateVersion 644 | tabOrder 646 | fieldName 648 | controlType 650 | staticText 652 | controlText 654 | numLines 656 | actionProfile 658 |
|---|---|---|---|---|---|---|---|---|---|
| Row 1 | Medication | 1 | 3 | MedRoute | 2 | Route | | 5 | MedRoute |
| 2 | Medication | 1 | 4 | MedFrequency | 2 | Frequency | | 5 | MedFrequency |
| 3 | Medication | 1 | 5 | MedType | 2 | Type | | 5 | MedType |
| 4 | Medication | 1 | 6 | MedPresmd | 3 | Prescribed By | | 1 | |
| 5 | Medication | 1 | 7 | MedSource | 2 | Provider Type | | 5 | MedSource |
| 6 | Medication | 1 | 8 | ActivityDataDue | 3 | StartDate | | 1 | AnyDate |
| 7 | Medication | 1 | 9 | ActivityDataDone | 3 | StopDate | | 1 | AnyDate |
| 8 | Medication | 1 | 10 | MedPrec | 2 | PreCert | | 3 | DmePrec |
| 9 | Medication | 1 | 11 | MedPrecdec | 2 | Decision | | 5 | DmePrecdec |
| 10 | Medication | 1 | 12 | ActivityNote | 4 | Comment | | 3 | |
| 11 | Medication | 1 | 0 | ActivityDescription | 2 | Medication Name | | 5 | MedName |
| 12 | Medication | 1 | 1 | MedDose | 3 | Dose | | 1 | MedDose |
| 13 | Medication | 1 | 2 | MedUnits | 2 | Units | | 5 | MedUnits |
| 14 | Disposition | 1 | 0 | ReferralSource | 2 | Referred From | | 5 | ReferralSource |
| 15 | Disposition | 1 | 1 | ExpectedDisp | 2 | Expected Disp | | 5 | ExpectedDisp |
| 16 | Disposition | 1 | 2 | ActualDisp | 2 | Actual Disposition | | 5 | ActualDisp |
| 17 | Disposition | 1 | 3 | CloseDate | 7 | Closed Date | | 1 | CloseDate |
| 18 | Disposition | 1 | 4 | ActivityAuthor | 3 | Recorded By | | 1 | |
| 19 | Disposition | 1 | 5 | ActivityNote | 4 | Note | | 5 | |

*700* Activity Records

*705* Medication Portion

| activityId | dose | frequency | medprec | medprecDec | medpresmd |
|---|---|---|---|---|---|
| 342 | 5g | every 4 hours | n | approved | Dr. Smith |
| 374 | 3g | every 6 hours | n | denied | Dr. Jones |
| 385 | 1000cc | hourly | y | approved | Dr. Jones |
| 399 | 500cc | every 2 hours | y | approved | Dr. Fuller |

*710* Common Portion

| activityId | templateName | templateVersion | whenEntered | author | calendarFlag | checkOffFlag | dateDone | cost | description | note | whenModified |
|---|---|---|---|---|---|---|---|---|---|---|---|
| 342 | Medication | 1 | 1997-02-12 10:11:33.000 | Paul Jones | N | N | 1997-02-12 | 0 | | | 1997-02-12 10:11:33.000 |
| 371 | Disposition | 1 | 1997-03-05 12:38:04.000 | Paul Jones | Y | N | 1997-03-05 | 0 | Compliance | | 1997-03-05 12:38:04.000 |
| 374 | Medication | 1 | 1997-03-05 16:14:18.000 | Paul Jones | N | N | 1997-03-05 | 0 | Compliance | | 1997-03-05 16:14:18.000 |
| 385 | Medication | 1 | 1997-07-06 15:23:25.000 | John Smith | N | N | 1997-08-15 | | | | 1997-08-15 12:13:24.000 |
| 394 | Disposition | 1 | 1997-08-09 08:34:23.000 | Paul Jones | Y | N | 1997-09-23 | | | | 1997-09-23 14:22:24.000 |
| 399 | Medication | 1 | 1997-09-23 11:32:45.000 | John Smith | N | N | 1997-09-30 | | | | 1997-09-30 15:32:33.000 |

*715* Disposition Portion

| activityId | actualDisposition | closeDate | expectedDisp | referralSource |
|---|---|---|---|---|
| 371 | 1997-05-05 | 1997-05-30 | 1997-05-05 | admit |
| 394 | 1997-09-01 | 1997-09-15 | 1997-08-27 | pcp |

800 PATIENT MENU

CarePartner–Case List (4 of 4)

File  Edit  Add  View  Tools  Options  Window  Help

Case List (4 of 4)

| Last | First | Activate Date | Case Id # | Group | Group# | Program | Next Review | Primary CM | Status | Dup |
|------|-------|---------------|-----------|-------|--------|---------|-------------|------------|--------|-----|
| Baker | Allison | 8/28/97 | 98765 | Pennsylvania | 8765 | 03-Low | 9/5/97 | Puckett | Active | |
| Brewster | Shari | 10/3/96 | 54378 | Employer15 | C23654 | Diabetes | 10/18/96 | Puckett | Active | |
| Kelley | Cleo | 10/9/96 | 54321 | Employer1 | 12345 | Diabetes | 10/20/96 | Puckett | Active | |
| Pentaudi | James | 9/22/96 | | Employer15 | EMP098 | Diabetes | 10/19/96 | Puckett | Active | |

Ready | Allen Puckett | 9:49 AM

FIG. 8B

CarePartner-(Baker, Allison)

File  Edit  Add  View  Tools  Options  Window  Help

*820* Patient Record

Patient | Case | Assess | Care Plan | Activities | Calendar | Contacts

SSN: 345-87-9945                Birthdate: 9/28/19        Age: 78
Subscriber #: 345879945-01      Death:
Gender: Female                  Martial: Married
Ethnicity: Caucasian            Language: English Phone:                          Address:
Home phone: (206) 345-1123        324 Pilgrim Road
Work phone: (206) 557-8978        Flourtown, PA 19031
                                  USA Group: Pennsylvania IPA         Group #: 8765
Employer: Heinz                 Rel Code: 00
Department: Marketing
Enroll Date: 3/27/97                                      Job Title: Graphic Artist
Hire Date: 5/17/91                                        Shift: Days
Next Review: 9/5/97

Ready                                         Allen Puckett    11:04 AM

FIG. 8C

840 Patient Record Edit Window

Enter Patient Info-Baker, Allison

| Last: | Baker | First: | Allison |
| SSN: | 345-87-9945 | Birthdate: | 9/28/19 |
| Subscriber #: | 345879945-01 | Death: | |

Gender: Female
Ethnicity: Caucasian
Marital: Married
Language: English

Phone: Work: (206)557-8978 x
Home: (206)345-1123
x

Address: 324 Pilgrim Road
Address 2:
City: Flourtown  St: PA  Country: USA
Zip: 19031

Group: Pennsylvania IPA
Employer: Heinz  Group #: 8765
Department: Marketing  Rel Code: 00
Enroll date: 3/27/97  Job Title: Graphic Artist
Hire date: 5/17/91  Shift: Days
Next Review: 9/5/97

OK — 842
CANCEL

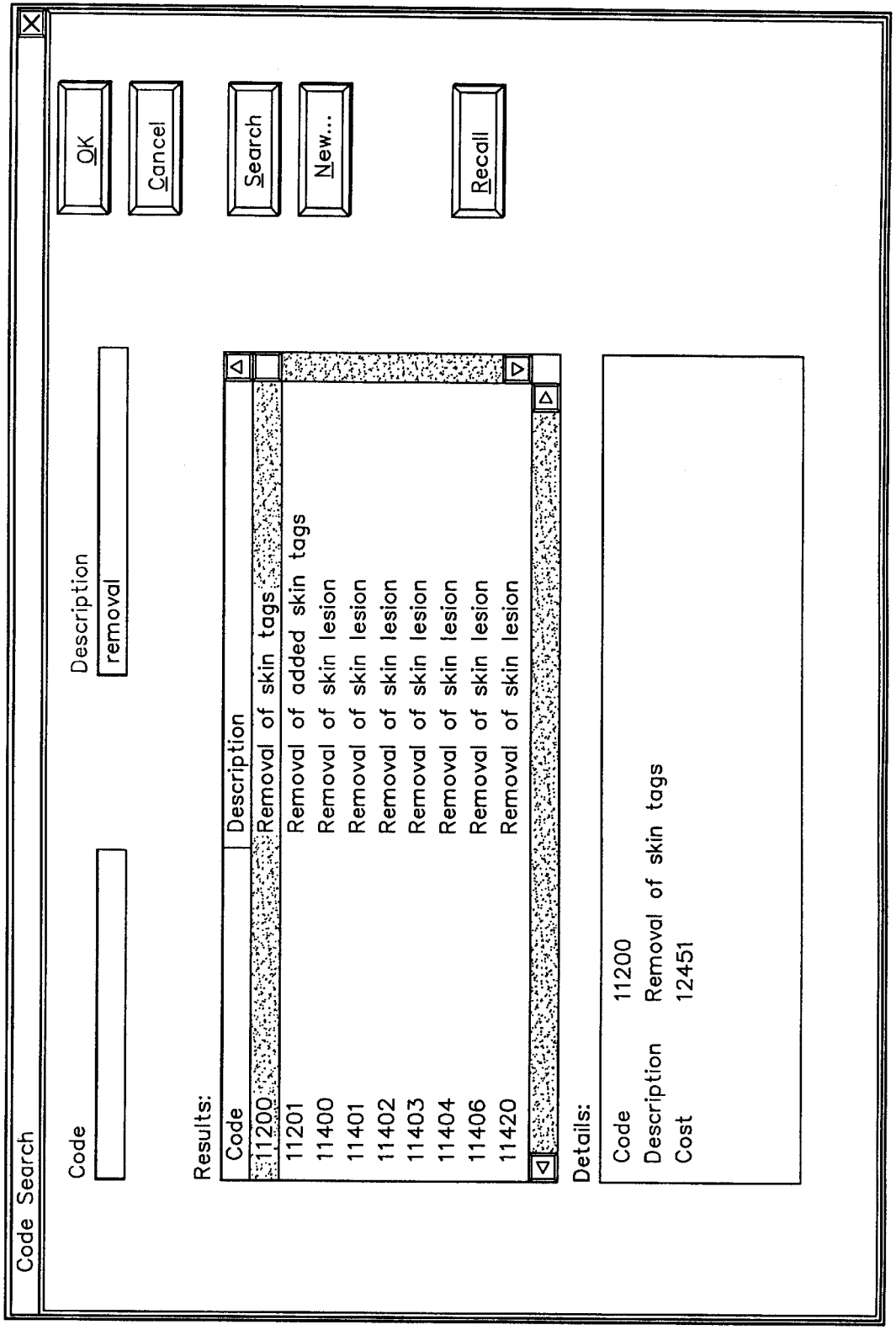
FIG. 8F1

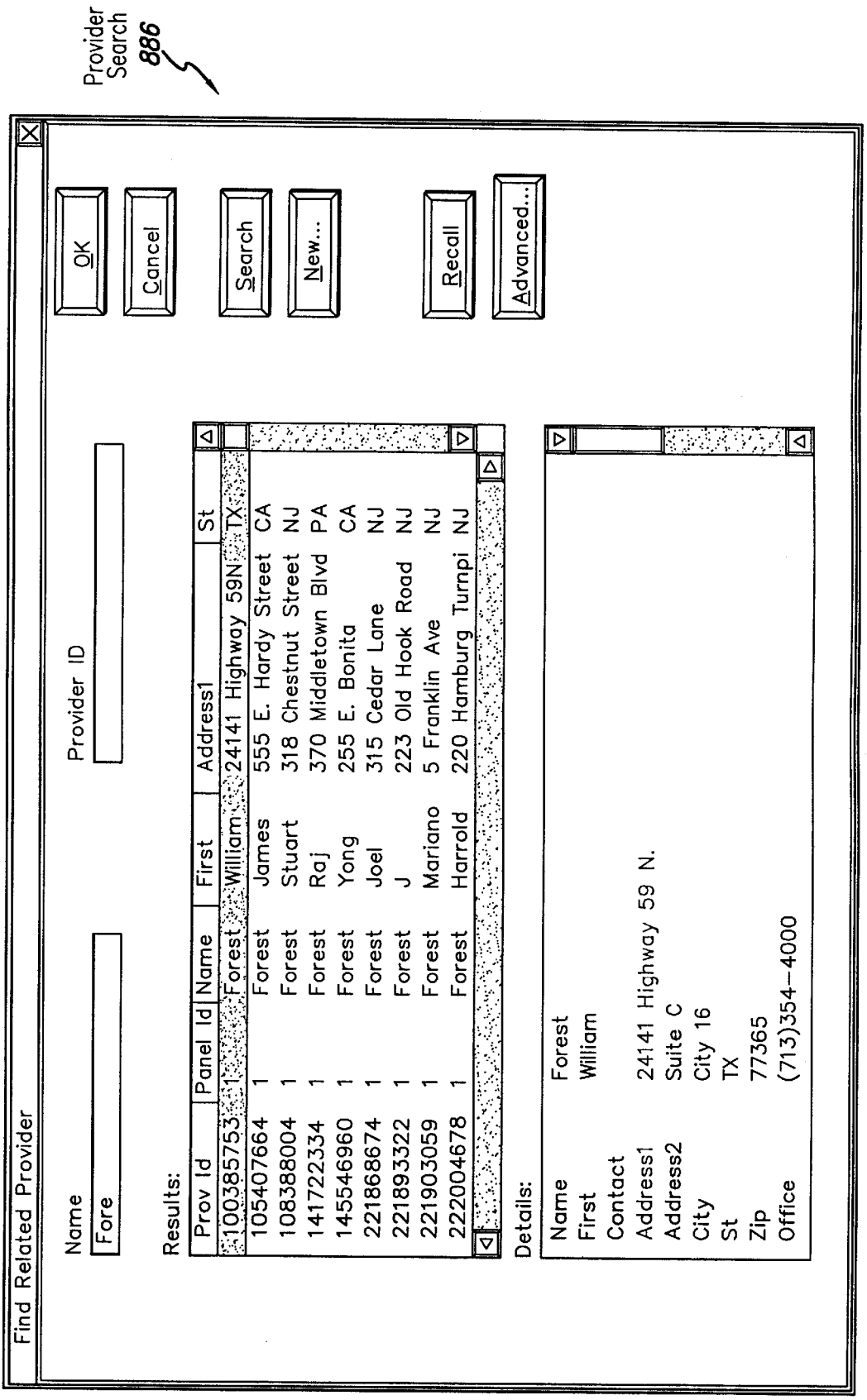
FIG. 8F2

FIG. 8F3
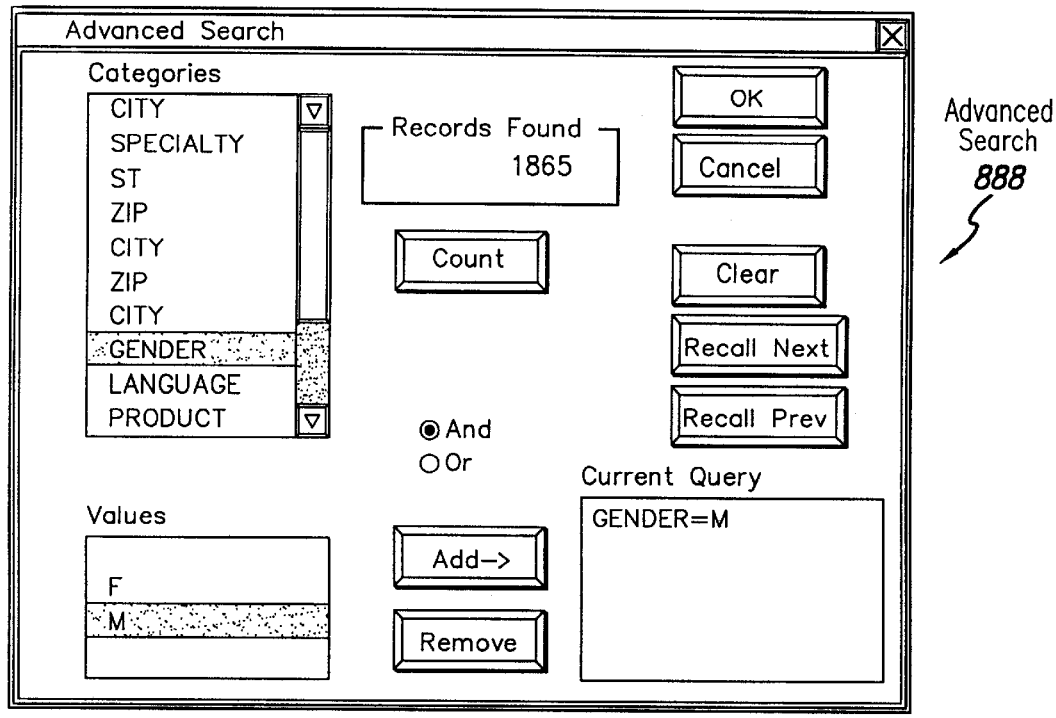
Advanced Search 888
FIG. 8H
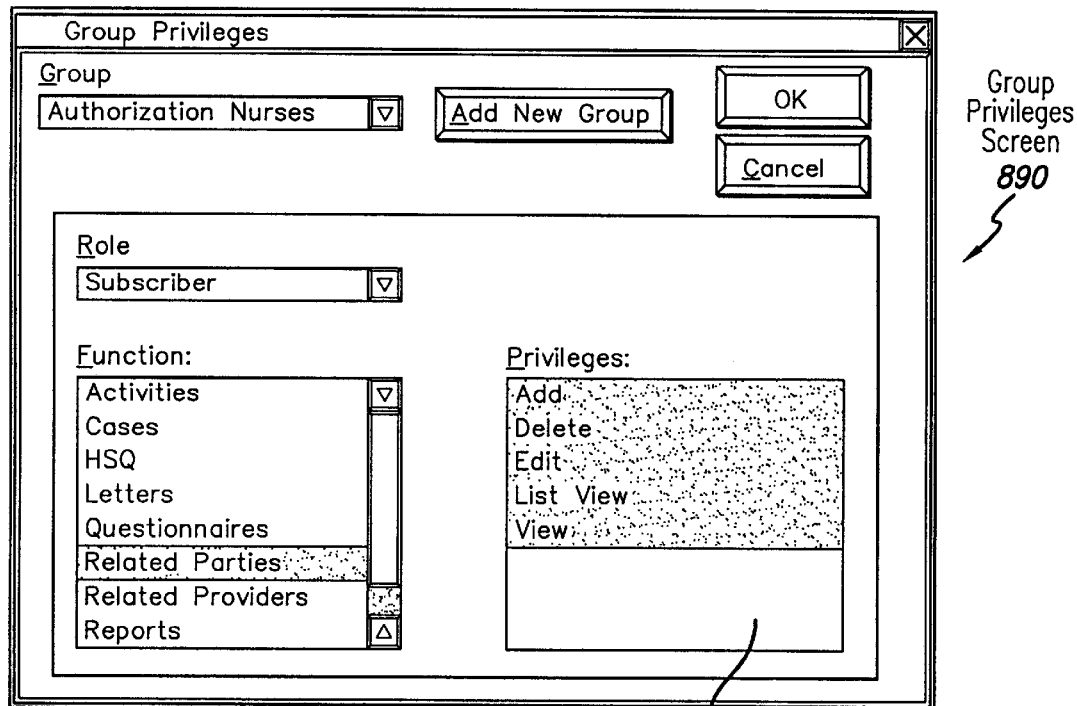
Group Privileges Screen 890

Medication Profile—Brewster, Shari

[Prev]  [Next]  Page 1 of 2  [OK]  [Cancel]

Medication Record Edit Window
882

Medication Name
Dose
Units
Route
Frequency
Start Date
Stop Date
Type

Medication Profile—Brewster, Shari

[Prev]  [Next]  Page 2 of 2  [OK]  [Cancel]

Med Source
Adv Reaction?
Describe

Recorded By  Allen Puckett

892 RESULTING CARE PLAN

Care Planning Step 4—Baker, Allison

Diagnosis:
Program: Respiratory
Type: Pediatric
Severity: Level I
Approach to Care: Care by PCP

| New | Date | Date Done | Phase | Activity | Inst | Description |
|---|---|---|---|---|---|---|
| | 9/11/97 | | Initial | Calendar: To Do/Reminder | | Phone Call To Follow-Up Init Letter |
| | 9/11/97 | | Initial | Calendar: To Do/Reminder | 1 | Respiratory Clinical Assessment |
| | 9/18/97 | | Follow-Up | Calendar: To Do/Reminder | 1 | Administer HSQ |
| | 9/18/97 | | Initial | Calendar: To Do/Reminder | 1 | Change Status to Active or Not Managed |
| | 9/18/97 | | Initial | Calendar: To Do/Reminder | 1 | Notify Physician of Program Enrollment Status |
| | 9/25/97 | | Follow-Up | Calendar: To Do/Reminder | 1 | Update Physician of Progress |
| | 8/28/98 | | Follow-Up | Calendar: To Do/Reminder | 2 | Administer HSQ |
| | 8/28/98 | | Follow-Up | Calendar: To Do/Reminder | 1 | Patient Satisfaction Survey |
| | 8/28/98 | | Initial | Calendar: To Do/Reminder | 2 | Respiratory Clinical Assessment |
| | 9/4/98 | | Follow-Up | Calendar: To Do/Reminder | 1 | Reevaluate plan of care |
| | 9/4/98 | | Follow-Up | Calendar: To Do/Reminder | 2 | Update Physician of Progress |

Cost  Requested $0.00  Approved $0.00

[Show]  [Cancel]  [< Back]  [Finish]

FIG. 8J

894 — Questionnaire

| | Baker, Allison—Initial Contact Survey | 10/7/97 | 9/30/97 | 5/21/97 |
|---|---|---|---|---|
| 1 | Initial Assessment Evaluation | | | |
| 2 | Present Treatments: | | | |
| 3 | Wound Care— | | | |
| 4 | Describe how the wound is cared for: | | | |
| 5 | Cleansing Agent | Hibiclens | Hibiclens | |
| 6 | Frequency | Q4hrs | Q8hrs | |
| 7 | Dressing Type | Kerlix Wrap | 4 X 4 | |
| 8 | Note | | Dressing | |
| 9 | Rehabilitation Therapy— | | | |
| 10 | Please check all that apply. | Speech | | |
| 11 | Mobility— | | | |
| 12 | Describe ambulation: | | | |
| 13 | Describe range of motion: | | | |
| 14 | Transfers | | | |
| 15 | Stair Climbing (are there stairs to climb?) | | | |
| 16 | Transportation— | | | |
| 17 | Is the patient driving? | | | |
| 18 | If not, is there anyone who can drive him/her? | | | |
| 19 | What mode of transportation is accessible? | | | |
| 20 | Living Dynamics— | | | |
| 21 | Please indicate ability level in ADL's: | | | |
| 22 | Does patient live with anyone? | | | |
| 23 | Is someone available to assist him/her in ADL's? | | | |
| 24 | Which of the following are accessible? | | | |
| 25 | Safety Measures: | | | |
| 26 | Is a fire extinguisher within reach? | | | |

SYSTEM AND METHOD FOR USING A RELATIONAL DATABASE TO ENABLE THE DYNAMIC CONFIGURATION OF AN APPLICATION PROGRAM

BACKGROUND OF THE INVENTION

1. Field of the Invention

The present invention relates to relational databases and database engines, and more particularly provides a system and method for using a relational database to enable the dynamic configuration of an application program, and even more particularly as it relates to the health care industry.

2. Description of the Related Art

Relational databases store information in tables which are linked together using key fields. Accordingly, a first table may contain a list of available menu items, for example, Item A, Item B and Item C. Additional tables, which correspond to the first table using the menu items as key fields, may contain lists of menu item fields. That is, Item A may correspond to a second table which contains Field A and Field B, Item B may correspond to a third table which contains Field C and Field D, and Item C may correspond to a fourth table which contains Field E and Field F. The purpose of menu Item A may relate to maintaining information on individual patients, the purpose of Field A may relate to maintaining the individual patient's name, and the purpose of Field B may relate to maintaining the individual client's social security number. It will be appreciated that the second table may include other fields relating to Item A, such as birth date, birth location, height, weight, etc. The patient information entered related to each of the fields for a particular menu item is referred to as a "record." For example, the information such as name, social security number, etc. relating to the individual patient is collectively a first record.

A database engine enables a user to peruse through the relational database and enables a user to apply search parameters or indexes to locate desired information in the relational database. Using the perusal search technique, the database engine retrieves the menu items and based upon its configuration specifies, for example, the appearance of the user interface, i.e., the font, color, size and location, the technique for selecting a menu item such as Item A, etc. Upon selection of a menu item, the database engine enables a user to view, select and modify each of the fields contained in the second table, namely, Field A and Field B, as specified by its particular configuration. For simplicity, each of viewing, adding, selecting, editing, etc. is referred to as "manipulating."

Using the parametric search technique, the database engine uses its particular configuration to prompt the user for parameters indicating a desired group of menu items (such as the menu items created after a particular date). The database engine compares the menu items and the fields of each menu item contained in the relational database against the selected parameters and generates the search results. Similar to the perusal technique, the database engine displays the results to the user also based on its particular configuration.

Using the indexing technique, the database engine need not perform a search, but need only locate the proper index identifying the grouping of menu items and fields desired. Again, the database engine enables the manipulation of items, fields and records according to the particular configuration of the database engine.

Regardless of the technique being used, the database engine manipulates records according to the predetermined configuration of the database engine. That is, the database engine is preset to display the data onto the display according to the font, color, organization, etc. as indicated by the database engine program. In order to modify the configuration characteristics of the database engine, the programmer must modify the database engine program itself. However, this is quite cumbersome process and takes a significant amount of time. Thus, manufacturers have avoided customizing application programs and in particular database engines. Therefore, a system and method are needed for using relational databases to dynamically configure an application program easily.

SUMMARY OF THE INVENTION

The present invention provides a system and method for using relational database structures to dynamically configure an application program. The system comprises first retrieving means such as an activities engine, a list view engine or a search engine for retrieving configuration data. The system further comprises second retrieving means such as the activities engine, the list view engine or the search engine for retrieving desired data such as patient or transaction records. The first retrieving means and the second retrieving means may each include the same engine. The system further comprises manipulation means such as the activities engine, the list view engine or the search engine for manipulating the desired data according to the configuration data.

For example, the list view engine may retrieve the column header information specifying the information that should be presented in the patient record window. The list view engine may then retrieve the desired records, possibly based on the results of a search by the search engine, and then present the patient record window including the desired records based on the configuration information retrieved.

The configuration information may be contained in a relational database. More particularly, first table means in the relational database may contain the desired data and second table means in the relational database may contain the configuration data. Accordingly, a database engine may more easily retrieve the data, and customization of the database may be a less cumbersome process.

Another system embodying the present invention comprises a relational database containing services for identifying a case manager, a first table for containing a menu item corresponding to the case manager, a second table coupled to the first table for containing patient data corresponding to the menu item, and a third table coupled to the first table and to the second table for containing configuration data corresponding to the menu item and to the patient data. The system further comprises an engine coupled to the relational database for using the configuration data to enable a user to manipulate the menu item and the patient data.

The method comprises the steps of retrieving configuration data, retrieving desired data, and manipulating the desired data according to the configuration data. The configuration information and the desired data may be contained in a relational database.

The system and method advantageously enable easy customization of a database. Instead of forcing a particular configuration based on the configuration of the application program accessing the data in the database, the configuration data is contained separately in the database. Accordingly, a application program common to all case managers can extract configuration data from the database and can use the extracted data to configure itself, thereby facilitating the customization of the application program.

BRIEF DESCRIPTION OF THE DRAWINGS

FIG. 6A is table illustrating an activity template;

FIG. 6B is a table illustrating an activity template field of an activity;

FIG. 6C is a table illustrating a field description of an activity template field;

FIG. 7 is a table illustrating activity records for the MEDS activity and the DISPOSITION activity;

FIG. 8A is a display screen view of a patient menu window;

FIG. 8B is a display screen view of a patient record of FIG. 8A;

FIG. 8C is a display screen view of a patient record edit window;

FIG. 8F1 is a display screen view of a generic search window;

FIG. 8F2 is a display screen view of a provider search window;

FIG. 8F3 is a display screen view of an advanced search window;

FIG. 8G is a display screen view of a medication record edit window;

FIG. 8H is a display screen view of a group provider screen window;

FIG. 8I is a display screen view of a resulting care plan;

FIG. 8J is a display screen view of a questionnaire;

DETAILED DESCRIPTION OF THE PREFERRED EMBODIMENTS

Figure 1:
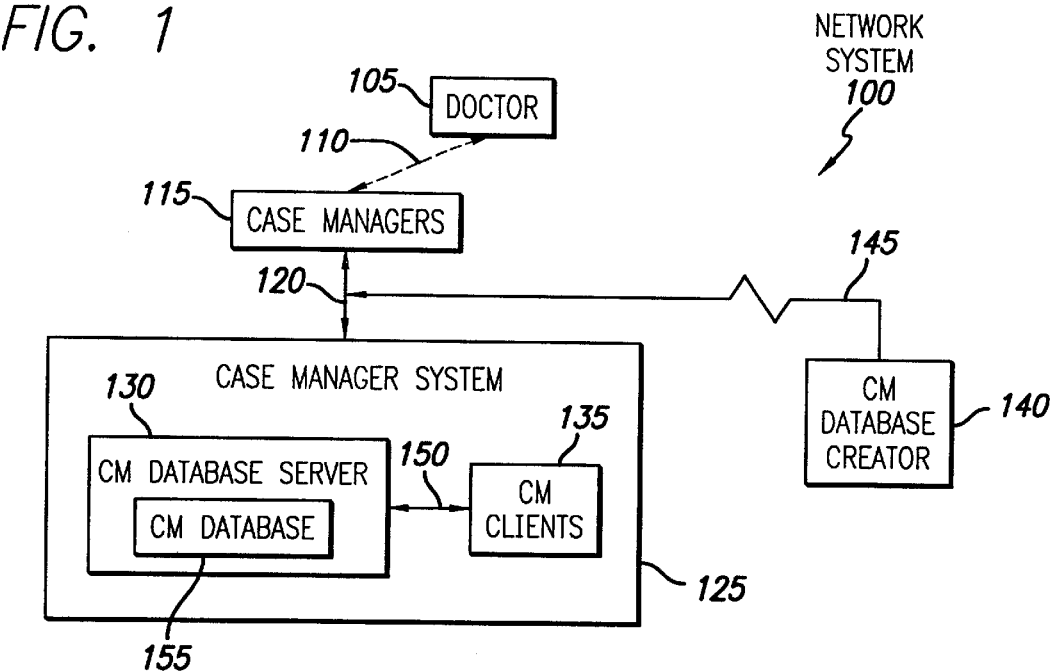
FIG. 1 is a block diagram illustrating an example network system in accordance with the present invention.

FIG. 1 is a block diagram illustrating an example network system 100 in accordance with the present invention. Network system 100 comprises a doctor 105 in communication with case managers 115 (i.e., persons who track the care of patients) via a first communications channel 110 such as a telephone line. The case managers 115 access a Case Manager (CM) system 125 via a second communications channel 120 such as a conventional graphical user interface. The CM system 125 includes a CM database server 130 and CM clients 135. The CM database server 130 stores a CM database 155, which contains configuration data 310 (described in detail with reference to FIG. 3) for configuring the CM clients 135 and patient data 305 (also described in detail with reference to FIG. 3). Further, a CM database creator 140 is coupled via a third communications channel 145 to the second communications channel 120, and enables the creation of the CM database 155 including the creation of the configuration data 310. One skilled in the art will recognize that communications channels 110, 120 and 145 may all be components of a single network system such as the Wide Area Network (WAN) commonly referred to as the Internet.

For example, a patient (not shown) goes to the doctor 105 complaining of specific symptoms, and the doctor 105 recommends a responsive care plan. The doctor 105 then contacts a case manager 115 assigned to this patient. The case manager 115 accesses the case manager system 125 to compare the doctor's recommendations against standard medical guidelines and against the patient's medical history, to prepare a response to the doctor 105, for example, accepting the care plan or recommending another, and to record the event. Because the configuration data 310 is stored in the CM database 155, the CM client 135 may be configured at run-time, i.e., during the boot-up of the client 135. It will be appreciated that the client 135 may be configured to authenticate the user, provide access to only a corresponding set of functions, provide access to only a corresponding list of patient records, display selected data in a desired arrangement, etc.

Figure 2A:
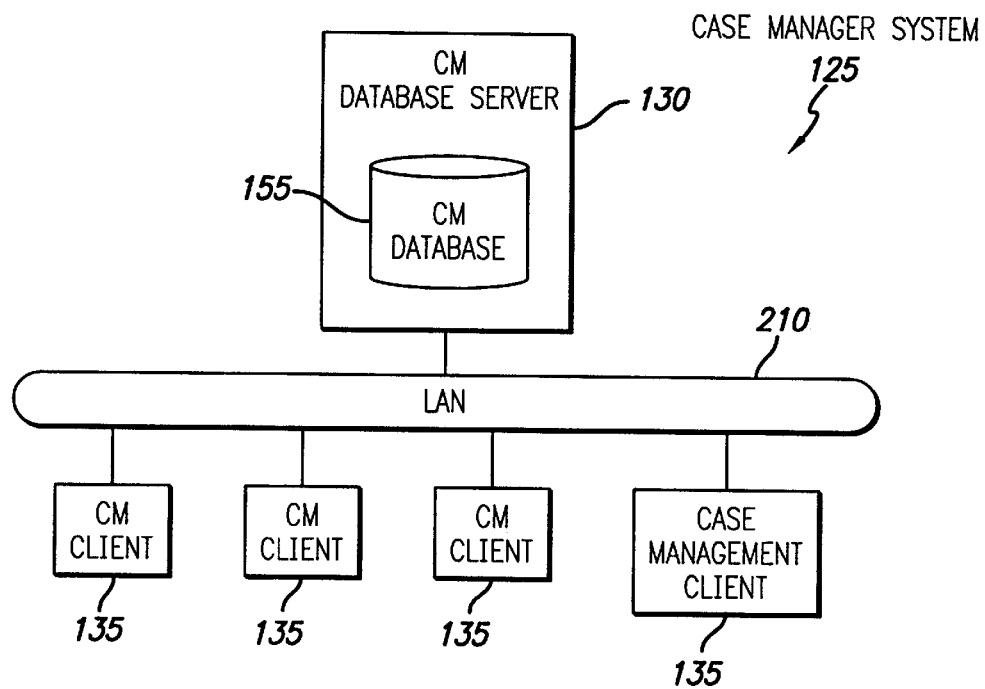
FIG. 2A is a block diagram illustrating details of the Case Manager (CM) system of FIG. 1.

FIG. 2A is a block diagram illustrating details of the CM system 125, which includes a CM database server 130 coupled via a Local Area Network (LAN) 210 to, for example, four CM clients 135. The CM database server 130 includes a CM database 155, preferably maintained in a relational database format and preferably storing patient data 305 and configuration data 310 (each described in detail with reference to FIG. 3). As illustrated, the CM database server 130 may be stored remotely from CM clients 135. Each of the CM clients 135 may access the CM database 155, for example, to review the patients medical history or to review the conventional medical guidelines. Each CM client 135 will be configured according to the configuration data 310 stored in the CM database 155 and thus will maintain a consistent appearance regardless of which terminal the case manager 115 uses.

Figure 2B:
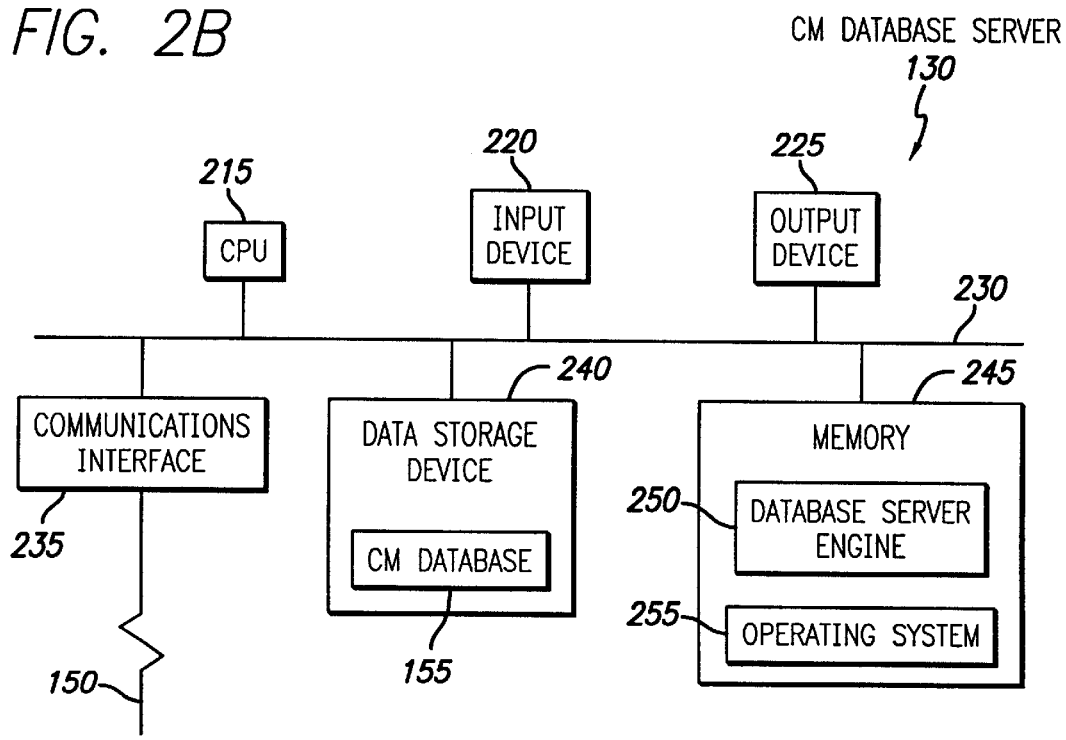
FIG. 2B is a block diagram illustrating details of the CM database server of FIG. 1.

FIG. 2B is a block diagram illustrating details of the CM database server 130 including a Central Processing Unit (CPU) 215 such as an Intel Pentium® microprocessor or a Motorola Power PC® microprocessor. An input device 220 such as a keyboard and mouse, and an output device 225 such as a Cathode Ray Tube (CRT) display are coupled via signal bus 230 to CPU 215. A communications interface 235, a data storage device 240 such as a magnetic disk, and memory 245 such as Random Access Memory (RAM) are further coupled via signal bus 230 to CPU 215. The communications interface 235 is coupled to communications channel 150 (FIG. 1), which may in turn be coupled to LAN 210 (FIG. 2A).

An operating system 255 includes a program for controlling processing by CPU 215, and is typically stored in data storage device 240 and loaded into memory 245 (as illustrated) for execution. The CM database 155 is stored in data storage device 240, but may alternatively be stored in memory 245. A database server engine 250 for accessing the CM database 155 may also be stored in data storage device 240 and loaded into memory 245 (as illustrated) for execution by CPU 215. Since the CM database 155 is being maintained as a relational database, the database server engine 250 preferably performs relational database management techniques for storing, searching and retrieving data from the tables of the CM database 155.

Figure 2C:
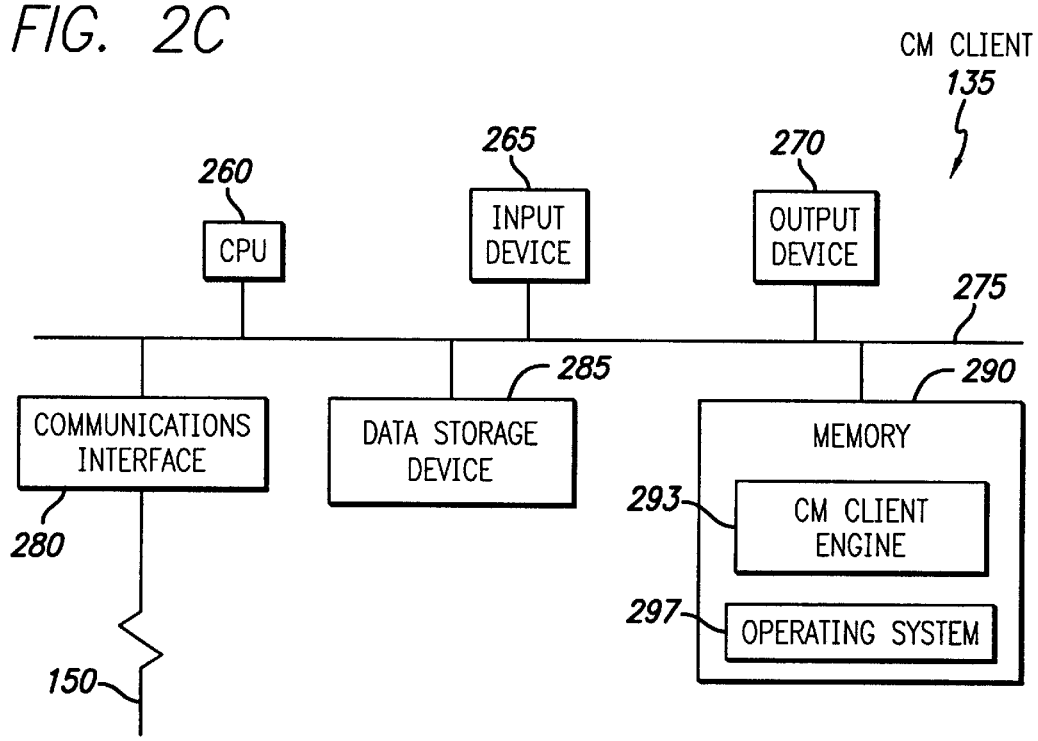
FIG. 2C is a block diagram illustrating details of the CM client of FIG. 1.

FIG. 2C is a block diagram illustrating details of an example CM client 135, which includes a CPU 260 such as an Intel Pentium® microprocessor or a Motorola Power PC® microprocessor. An input device 265 such as a keyboard and mouse, and an output device 270 such as a CRT display are coupled via signal bus 275 to CPU 260. A communications interface 280, a data storage device 285 such as a magnetic disk, and memory 290 such as RAM are further coupled via signal bus 275 to CPU 260. The communications interface 280 is coupled to communications channel 150 (FIG. 1), which may in turn be coupled to LAN 210 (FIG. 2A).

An operating system 297 includes a program for controlling processing by CPU 260, and is typically stored in data storage device 285 and loaded into memory 290 (as illustrated) for execution. A CM client engine 293 for managing the CM database 155 remotely may also be stored in data storage device 285 and loaded into memory 290 (as illustrated) for execution by CPU 260.

Figure 3:
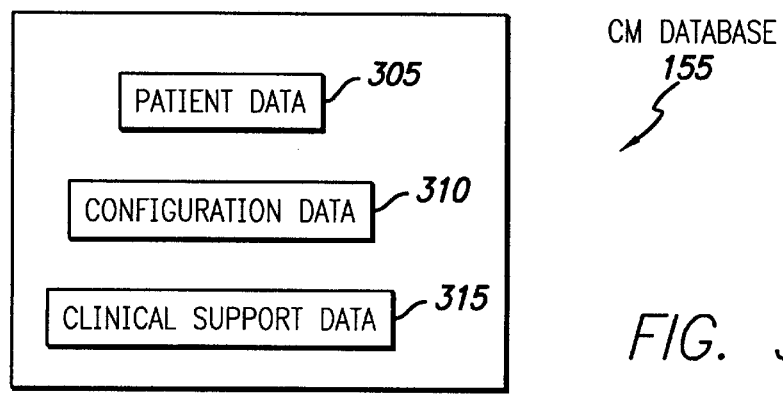
FIG. 3 is a block diagram illustrating details of the CM database of FIG. 2B.

FIG. 3 is a block diagram illustrating details of the CM database 155. The CM database 155 contains patient data 305, which includes patient records for each of the patients assigned to the case managers 115 accessing the particular database 305. The patient data 305 is preferably maintained in a relational database format, and may be divided into common records and extension records. The division of data 305 into common and extension records is described in detail with reference to FIG. 7.

The CM database 155 further includes configuration data 310. The configuration data 310 contains information indicating the menus, activities, records, etc. available to the case manager 115 accessing the CM database 155. The configuration data 310 may further include information indicating the fields to be included in each of the menus, activities, records, etc. Accordingly, the configuration data 310 controls the data needed for input, display and modification of patient records 305, field descriptions and dialog fields. The configuration data 310 is also preferably maintained in a relational database format, i.e., in tables. Examples of the configuration data 310 are illustrated in FIGS. 6A, 6B, 6C and 7.

The CM database 155 further includes clinical support data 315. The clinical support data 315 includes information available for comparison with the medical care plan recommended by the doctor 105. Examples of clinical support data 315 include conventional clinical guidelines and code sets for addressing the patient's symptoms.

Figure 4:
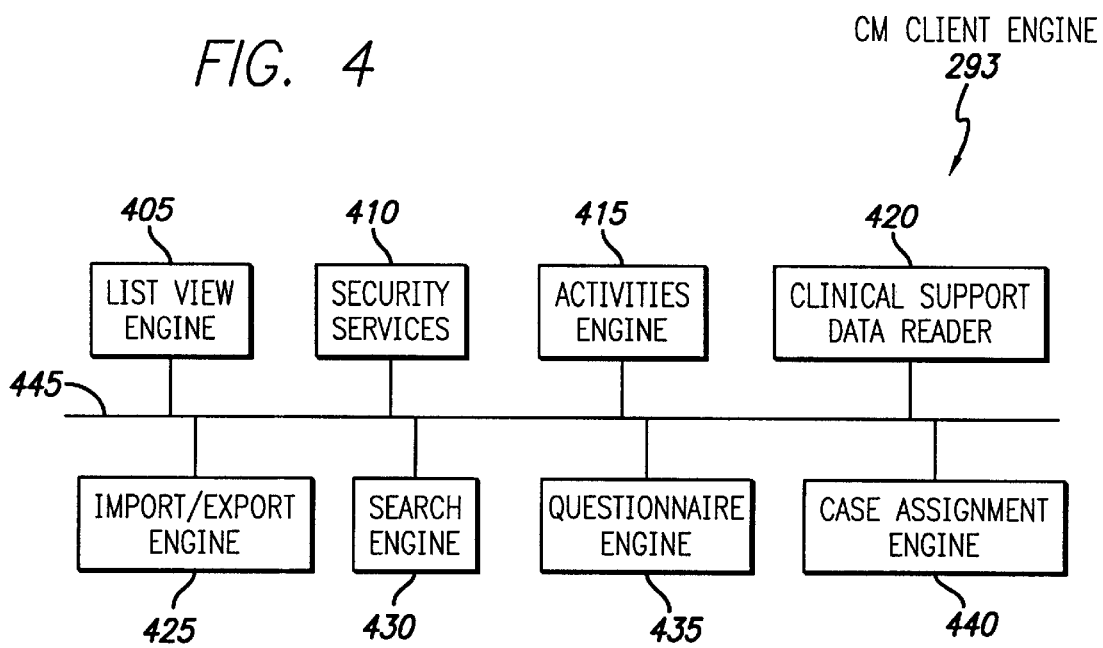
FIG. 4 is a block diagram illustrating details of the CM client engine of FIG. 2C.

FIG. 4 is a block diagram illustrating details of the CM client engine 293. The CM client engine 293 includes a list view engine 405, security services 410, an activities engine 415, a clinical support data reader 420, an import/export engine 425, a search engine 430, a questionnaire engine 435 and a case assignment engine 440. Although each of these elements is illustrated as coupled to a signal bus 445, one skilled in the art will recognize that the connections are merely software based.

The security services 410 identify and authenticate the case manager 115 accessing the CM database 155, for example, using a case manager identification number and a password. Upon authentication, the security services 410 obtain the configuration data 310 indicating the menus, activities, patients, etc. corresponding to the case manager's privileges. The security services 410 allow easy ad hoc specification of individual roles and group memberships, as well as the specification of privileges (based on role and group membership) with respect to entry, edit and view. The security services 410 are then used to enforce the security privileges. An example group privileges screen 890 is illustrated in FIG. 8H. Namely, the group "authorization nurses" lists the case managers 115 authorized to access the CM database 155. The role indicates whether the case manager 115 is a subscriber or owner (each providing different privileges. The function list indicates the available functions that the case manager 115 can access. Selecting a case manager 115 function provides in the privileges window 891 a list of actions authorized to the case manager 115.

The clinical support reader 420 enables the case manager 115 to read the clinical support data 315, and to compare the clinical support data 315 against the doctor's recommended care plan. After the case manager 115 compares the clinical support data 315 and the recommended care plan, the case manager 115 can generate a resulting care plan. An example resulting care plan is illustrated in FIG. 8I.

The questionnaire engine 435 enables the case manager 115 to prepare a report of the patient's symptoms. For example, the questionnaire engine 435 lists possible questions to ask the patient, and enables the case manager 115 to input the responses into a questionnaire screen. An example questionnaire screen 894 is shown in FIG. 8J. The questionnaire screen 894 is configurable using the configuration data 310 described with reference to FIG. 3 and with reference the remaining figures.

The search engine 425 enables the case manager 115 to prepare a query for searching the CM database 155. Preferably, the search engine 430 dialogs the case manager 115 for search parameters and compiles the parameters into an SQL query. An example generic search window 884 is illustrated in FIG. 8F1. An example provider search window 886 is illustrated in FIG. 8F2. An example advanced search window 888 is illustrated in FIG. 8F3. The search engine 430 then communicates with the database server engine 250, which searches the CM database 155. For example, the case manager 115 may select the parameters for the patients assigned to case manager John Smith and admitted to James Hospital after Jan. 1, 1997.

The list view engine 405 enables the case manager 115 to view lists of records of the patient data 305 assigned to the case manager 115 according to the search results of the search engine 430. The list view engine 405 uses the configuration data 310 to configure the user interface and the data being displayed. The list view engine 405 preferably operates entirely on dynamically defined data determining the content, column headers, sort and filter qualities of each list at run-time.

The case assignment engine 440 examines the case data and determines which case manager 115 should be given the assignment. The determination may be made based on the patient, the hospital, available case manager staff, the date admitted, etc. The case assignment engine 440 can be configured to use a parameter such as any fields from the case, for example, case, patient and assessment tabs (including customized data) along with a number of comparison and arithmetic operators.

The activities engine 415 determines which activities such as medication summaries, patient discharge summaries, assessment results, care plan variance summaries, etc. exist, determines which activities are available, enables the case manager 115 to select one of the available activities, enables the case manager 115 to select one of the available activity fields such as the start date of a medicinal program, enables the case manager 115 to enter new data into the activity record, etc.

The import/export engine 425 translates records to and from another format, such as the Health Level Seven format or the ANSI X.12 format. The import/export engine 425 can import and export base and customized data (i.e., data defined by a customer and not known to the application prior to run-time). The import/export engine 425 preferably uses mapping tables. Should any additional configuration data 310 be needed, the import/export engine 425 either requests the information from the user or uses predetermined default values. If the original format has additional data unnecessary for the intended format, the import/export engine 425 discards the data 310.

It will be appreciated that the elements of the CM client engine 293 are configured according to the configuration data 310. That is, the activities engine 415 may retrieve configuration data 310 specifying, for example, the available activities, configuration data 310 indicating the fields in each activity, configuration data 310 indicating predetermined characteristics of the user interface, e.g., the location for viewing the available activities, the order the activities are placed, etc. Examples of the configuration data 310 are shown in FIGS. 6A, 6B, 6C and 7. Examples of screen shot views of the user interface are illustrated in FIGS. 8A, 8B, 8C, 8D and 8E. The activities engine 415 effectively retrieves the configuration data 310 from the tables of the CM database 155.

The tables being used to implement the elements of the CM client engine 293 of FIG. 4 are listed.

| Tables for Activities Engine | | | | |
|---|---|---|---|---|
| Activity | | | | |
| activityId | templateName | templateVersion | whenEntered | author |
| ActivityTemplate | | | | |
| templateName | templateVersion | description | category | calendarFlag |
| ActivityTempltFld | | | | |
| templateName | templateVersion | tabOrder | fieldName | controlType |
| FieldDescription | | | | |
| fieldName | abbrLabel | shortLabel | longLabel | locationType |
| DialogFields | | | | |
| dialogId | fieldId | fieldName | labelType | fieldType |
| Tables for Questionairre Engine | | | | |
| Questionnaire | | | | |
| qstnnId | qstnnType | qstnnHdrFntName | qstnnftdrFntSzQty | qstnnHdrFntClrId |
| QuestionnaireType | | | | |
| qstnnTypeId | qstnnTypeName | qstnnTypeInsertTs | | |
| QinQ | | | | |
| qstnnId | qstnTd | qInOrderQty | qinqAnsSQLColName | qInQInsertTS |
| Question | | | | |
| qstnId | qstnType | qstnLeftId | qstnRightId | qstnText |
| QuestionType | | | | |
| qstnTypeId | qstnTypeName | qstnTypeInsertTS | | |
| ControlType | | | | |
| controlTypeId | controlTypeName | | | |
| DataType | | | | |
| dataTypeId | dataTypeName | dataTypeInsertTS | | |
| SkipAction | | | | |
| qstnId | domExtId | skipSectionInd | skipToQuestionId | skipInsertTS |
| Domain | | | | |
| domainId | domainName | domainDataType | domainScaleQty | domainWidthQty |
| DomainExtension | | | | |
| domExtId | domainId | domExtOrderQty | domExtInsertTS | domExtCaptionText |
| Tables for Security Services | | | | |
| CaseManager | | | | |
| cmId | nameLast | nameFirst | loginId | cmDeactivatedFlag |
| GroupMembership | | | | |
| cmId | secGroupId | grpMemAssignedById | grpMemInsertTS | |
| GroupRole | | | | |
| secGrpRoleId | secRoleId | secGroupId | grpRoleInsertTS | |
| GrpRolePriv | | | | |
| secGrpRoleId | privCtxtId | grpRolPrivInsertTS | | |
| PrivilegeForContext | | | | |
| privCtxtId | privCtxtDbId | secContextId | secContextDbId | secPrivilegeId |
| ValidPrivilege | | | | |
| secRoleId | privCtxtId | valPrivInsertTS | | |
| SecurityContext | | | | |
| secContextId | secContextDbId | secContextName | secContextTxt | secSubContextName |
| SecurityGroup | | | | |
| secGroupId | secGroupDbId | secGroupName | secGroupInsertTS | secGroupUndeleteFlag |
| SecurityPrivilege | | | | |
| secPrivilegeId | secPrivilegeDbId | secPrivilegeName | secPrivilegeTxt | secPrivilegeInsertTS |

-continued

```
SecurityRole
secRoleId          secRoleDbId      secRoleName      secRoleDisplayTxt    secRoleInsertTS
Tables for List View Engine ListViewColumns
name               colOrder         colName          header               showit
ListViewQuery
name               description      category         selFrom              selWhere
MenuConfiguration
mcId               mcText           mcTypeName       mcContextName        mcApplicCtxtName
Tables for Case Assignment Engine TriageRule
Sequence           cmId             status           trulReqApproveFlag
TriageRuleItem
Sequence           ColName          RuleItem
TriageRuleModel
Sequence           Hard             RuleColumnName   TableName            FieldName
Tables for Search Engine ProviderMaster
ConfigTables.doc
pvdrMstrId         providerId       panelId          whenAltered          whenModified
ExtendedInfo
providerId         panelId          infoName         infoValue
ValidValues
validName          validValue       vvalSeqQty
code_table
proc_code          code_description
Tables for Clinical Support Data Reader (Care Plan Wizard)

CarePlanTemplate
name               description      comments         guideline
CarePlanActivities
name sequence templateName quantity startDateIx startDelta repeatDateIx repeatDelta calendarFlag checkOffFlag cost descriptio
Tables for Import/Export Engine ImportDataMap
Idx Msg Evt Segment FieldNum Rep Type SubTypeID TranTblID Entity Container Width Offset CrtFlag
ImportRules
Idx RuleID Entity Container Literal Operator
ExportDataMap
Idx Msg Evt Segment FieldNum Rep Type SubTypeID TranTblID Entity Container Width Offset CrtFlag RuleID
ExportRules
Idx RuleID Entity Container Literal Operator
TranslationMap
Idx TableID KeyTxt LiteralTxt OperatorTxt
```

Figure 5:
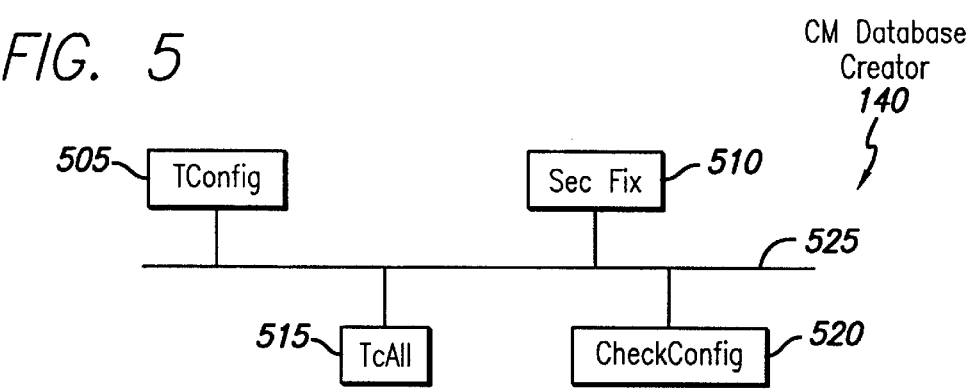
FIG. 5 is a block diagram illustrating details of the CM database creator of FIG. 1.

FIG. 5 is a block diagram illustrating details of the CM database creator 140. The CM database creator 140 includes a TConfig tool 505, a SecFix tool 510, a TcAll tool 515 and a CheckConfig tool 520. Although each of these tools are illustrated as coupled together via a bus-type structure 525, one skilled in the art will recognize that the connections are software based.

The Tconfig tool 505 may read and translate a text file into an SQL file that may be used to build activities and list views. A compatible tool provided by the CM database vendor can be used to execute the SQL file on the CM database 155. For example, the Sybase SQL Central Program, can be used to apply these files to a Sybase SQL Anywhere database. The TcAll tool 515 may be used to automate the execution of the Tconfig tool 505 on a series of source files. The SecFix tool 510 reads security-related portions of the configuration data 310 in the CM database 155 to identify errors for the user and to correct privileged configuration data 310. The CheckConfig tool 520 reads the activities-related portions of the configuration data 310 in the CM database 155 to identify errors for the user.

FIG. 6A illustrates an activity template table 600. The activity template table 600 includes columns for a template name 605, a template version 610, a description 615, a category 620, a calendar flag 625, a CheckOff flag 630 and cost 635. Each activity template preferably describes how to enter, store, and present one record of one type of data. The activity template table 600 illustrated contains two activities, namely, "Medication" in row one and "Disposition" in row two. The Medication activity corresponds to template version "1," description "Medication Profile," category "CarePlan," calendar flag "N," CheckOff flag "N" and cost "0." The Disposition activity corresponds to template version "1," description "Case Disposition," category "System," Calendar flag "N," CheckOff flag "φ" and cost "0."

More particularly, the Medication activity parameters of the activity template table 600 define the configuration data 310 that the activities engine 415 uses to configure. That is, from these parameters, the activities engine 415 determines that the medication activity exists. The activities engine 415 further determines that the specified Medication activity template is a first version ("1") of the template. The version number enables the activities engine 415 to manage changes to the template at run-time by matching the version of the fields with the version of the template. The activities engine 415 displays the description "Medication profile" to describe the particular activity to the user, and knows to place this activity in the category "CarePlan" so that the user can find the activity. Further, because the Calendar flag is off, the activities engine 415 does not display activity dates, such as medication start date medication stop date, on the electronic calendar. Because the CheckOff flag is currently on, the activities engine 415 enables the medication activity to be "Checked-Off" using the check-off toolbar button or edit activity status. Further, the activities engine 415 determines that the cost for this activity is "0." It will be appreciated that the activities engine 415 applies the Disposition activity parameters in a manner similar to that of the Medication activity.

FIG. 6B is a table illustrating activity template fields table 640 for the Medication and Disposition activity template table 600. More particularly, rows 1–13 pertain to the Medication activity of template table 600, and rows 14–19 pertain to the Disposition activity of template table 600. Activity template fields table 640 includes columns for a template name 642, a template version 644, a tab order 646, a field name 648, a control type 650, static text 652, control text 654, the number of lines 656 and an action profile 658.

The template name identifies the activity as specified in the activity template table 600. The template version 644 corresponds to the version of activity being requested. Thus, the template version 644 will indicate the if an activity has been added or updated. Tab order 646 specifies the display order of each of the fields within each activity. Namely, for the Medication activity, the first field to be displayed is "Activity Description" in row 11. The display order continues with rows 12, row 13 and then rows 1–10 sequentially. The field name 648 identifies each of the fields by a unique identifier. For example, row 13 is identified as "MedUnits."

The control type 650 identifies the type of user interaction, such as edit, pick list, button, static text, etc. to be used when accepting data from a user upon request. That is, when the case manager system 125 prompts the case manager 115 for data specifying the patient's name, the activities engine 415 will present an edit control that will accept a free-form text string (which may be identified as control type "3.") The static text 652 identifies the string of text that will be presented to the case manager 115 to label the control 650 on the output device 270 when viewing or requesting input of data. Should the control type be a control requiring text, for example, a button, control text 654 is the text presented to the user at run-time. For example, if a search on a set of codes is configured on a button, the control text might be "search code." The number of lines 656 describes the number of lines to display for data entry. For example, for a large field of 2000 bytes, the number of lines 656 may be set to "5" or "6" to enable the user to view more text without scrolling. Lastly, the action profile 658 references a segment of the program initialization file that may contain additional configuration information, for example, ranges for numeric values.

FIG. 6C illustrates a field description table 660, related to the activity template fields table 640 using the field name 648 as the key field. Field description table 660 includes columns for the field name 662, an abbreviated label 664, a short label 666, a long label 668, a location type 670, a location name 670 and a real name 674.

Thus, when the activity engine 415 provides the case manager 115 with a display screen for, for example, the field medical dose (FIG. 6B, row 12), the activities engine 415 will locate related field description table 660 (FIG. 6C), will identify row 1 as having the same field name 662, and will provide a user interface as specified by the columns. That is, if the activities engine 415 requests a long label to fully describe the data being viewed, requested, etc., the activities engine 415 will locate column 668, and will retrieve the label "Medication Dosage." Alternatively, should the activities engine 415 request only a short label, then the activities engine 415 will locate column 666, and will retrieve the label "Dosage."

The location type "SQL" defines the type of location where the referenced field is located. For example, "SQL" implies that the field is stored in a relational-type CM database 155. The real name 674 identifies the database field where the referenced data is stored. The location name 672 identifies the database table where the referenced data is stored. For example, the medication dose (row 1) will be stored in the dose field of the medication table.

FIG. 7 illustrates activity records 700 contained in the case manager database 155. As illustrated, an activity record 700 can be contained in multiple tables. For example, a first medication record is contained in medication portion 705 having activity identification "342" (row 1, column 720) and in common portion 710 also having activity identification "342" (row 1, column 732). Similarly, the first disposition record is contained in the disposition portion 715 having activity identification "371" (row 1, column 760) and in common portion 710 also having activity portion "371" (row 1, column 732). Using a common portion 710 avoids creating additional tables, which can be shared among different records. Using a common portion 710 thus saves memory and facilitates customization. It will be appreciated that the medication portion 705 and the disposition portion 715 are each referred to as an "extension portion."

The medication portion 705 includes columns for activity identification 720, dose 722, frequency 724, medprec 726, medprecDec 728, and medprecmd 730. As stated above, the activity identification 720 identifies the record and acts as the key field to link it with the common data in the common portion 710. The dose 722 indicates the medication dosage prescribed by the doctor 105. The frequency 724 indicates how often the prescribed medication should be ingested. The medprec 726 is a flag indicating whether the medication required precertification. The medprecDec 728 is a flag indicating whether the prescribed medication has been approved or denied by the case manager 115. The medprecmd 730 identifies the doctor 105 prescribing the medication.

The disposition portion 715 includes columns for activity identification 760, actual disposition 762, closure date 764, expected disposition 766 and referral source 768. The activity identification 760 identifies the disposition record. The actual disposition 762 identifies the date of patient discharge. The close date indicates the date of the case closure. The expected disposition 766 indicates the date of expected patient discharge. The referral source 768 indicates the source that referred the patient to the case manager 115.

The common portion 710 includes columns for activity identification 732, template name 734, template version 736, when entered 738, author 740, calendar flag 742, checkOff flag 744, dateDone 746, cost 748, description 750, note 752 and when modified 758. The activity identification 732 identifies the activity record. The template name 734 identifies the activity template 600 used to manipulate the record. The template version 736 indicates the version of the activity template 600 that created it. When entered 738 indicates the date the record was created. The author 740 identifies the case manager 115 that opened the record. The calendar flag 742 indicates whether the dates of the record should be presented by the activities engine 415 on a calendar. The checkoff flag 744 indicates whether the activity is to be checked-off using the check-off toolbar button. The dateDone 746 indicates the date the activity was checked-off or completed. The cost 748 indicates billing information for the activity. The description 750 specifies the summary description of the activity. The note 752 is a long description associated with the activity. When modified 758 indicates the date when the record was last modified. Accordingly, the case manager 115 can recognize inactive records.

Each of these columns are shared among the medication records and the disposition records. Upon selection of a record, the activities engine 415 will extract the data from the common portion 710 and from the extension portions 705 and 715. For example, when selecting a medication activity, data is extracted from the common portion 710 and from the medication extension 705.

FIG. 8A is a display screen view of an example patient menu 800. The menu 800 lists records for "Baker," "Brewster," "Kelley," and "Pentaudi," and includes each patient's last name, first name, activation date, case identification number, group number, program, next review date, primary case manager 115 and status. The columns illustrated in the menu are determined by the configuration information in the tables. That is, the configuration data in the tables indicate that the menu 800 should display the columns illustrated.

FIG. 8B is a display screen view of a patient record 820. The record 820 lists available fields for patient information, case information, assessment information, care plan information, available activities, calendar information and contact information. The record currently illustrates patient information, namely, social security number, birthdate, age, subscriber number, gender, ethnicity, etc. Again, the information displayed is controlled by configuration information in the tables.

FIG. 8C is a display screen view of a patient record edit window 840. The edit window 840 includes a title bar with "Enter Patient Info—Baker, Allison." The edit window 840 also includes a description of the information needed, such as "Last:," and a field with the last name of the patient "Baker." Further, in some instances, the edit window 840 includes a description of the information needed, such as gender, and includes a pick list ("male" or "female") with the selected pick "female" illustrated.

Figure 8D:
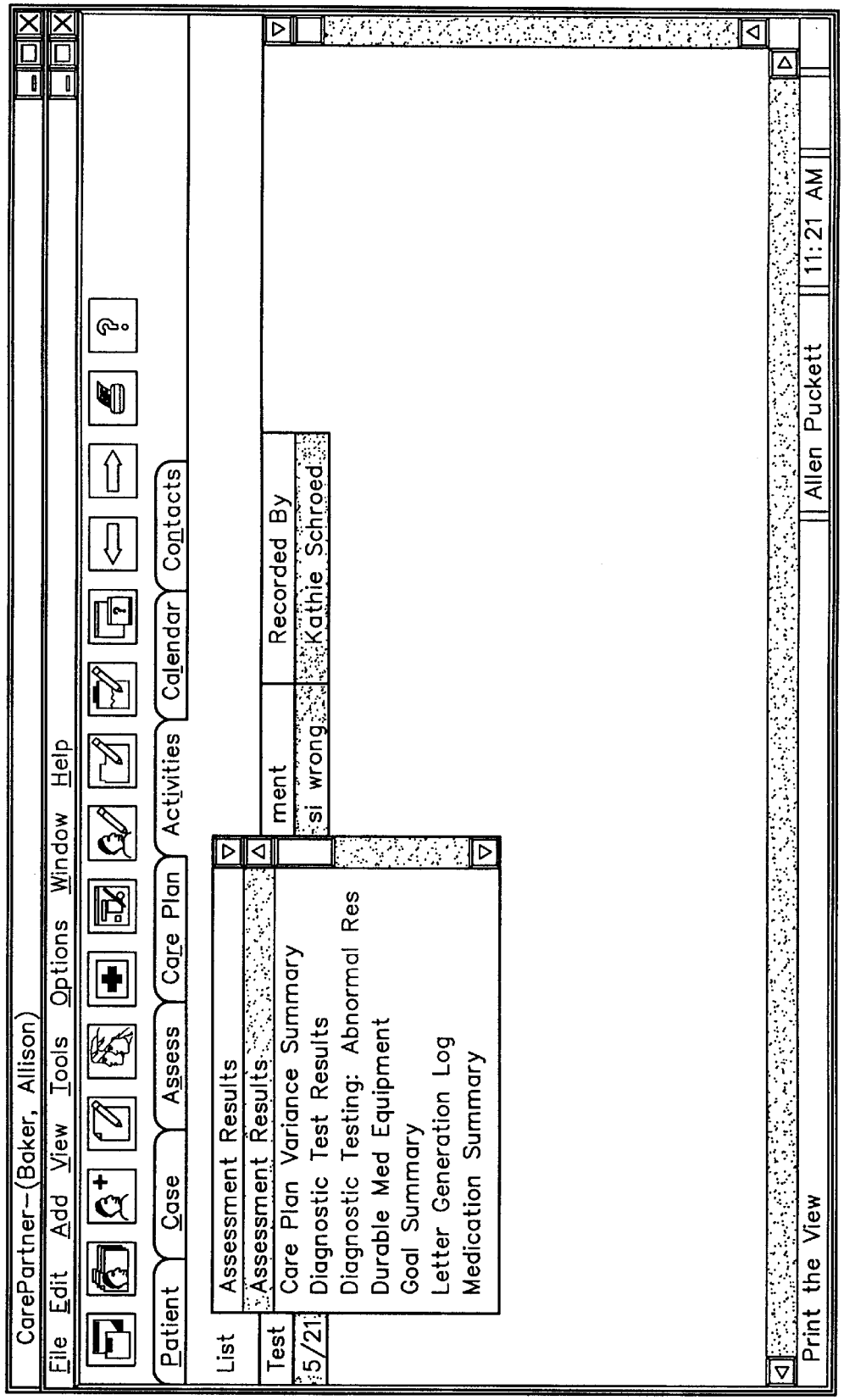
FIG. 8D is a display screen view of an activity pick-list menu.
Figure 8E:
FIG. 8E is a display screen view of the activity list field for the MEDICATION SUMMARY activity.

FIG. 8D is a display screen view of an activity list 860, which includes a list of available activities, namely, assessment results, care plan variance summary, etc. The list of activities is again indicated by the tables. An example activity table is shown in FIG. 6A. Selection of one of the activities provides activity list fields 880 shown in FIG. 8E. FIG. 8E is a display screen view of the activity list fields 880 for the medication summary activity. The columns illustrated include medication name, dose, units, route, frequency, start date, stop date, medication type, provider name, adverse reactions, and description. The columns displayed are controlled by a list view table, which is similar to the activity fields table 640 illustrated in FIG. 6B.

Figure 9:
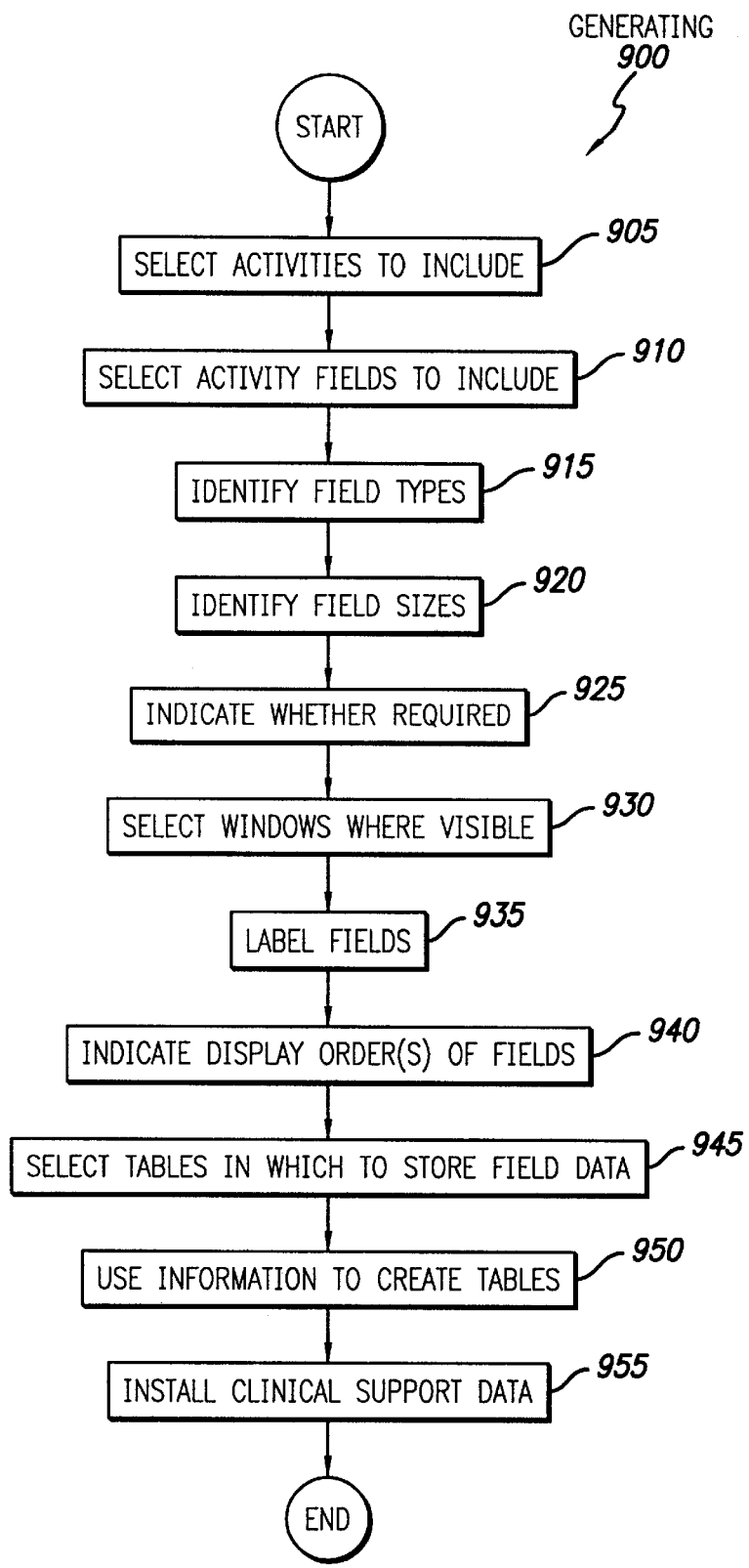
FIG. 9 is a flowchart illustrating a method for generating a relation database configuration table.

FIG. 9 is a flowchart illustrating a method 900 for generating, for example, configuration data 310 for the activities. Method 900 begins with a user via the case manager database creator 140 in step 905 selecting activities and in step 910 selecting the activity fields for each activity to include in the CM database 155. The user in step 915 identifies the field types and control types 650 (see FIG. 6B), and in step 920 identifies the field sizes and numLines 656 (see FIG. 6B). The user in step 925 indicates whether data for each the activity fields are required when the case manager 115 is entering a patient record 820. The user in step 930 then selects, for example, the window where the case manager 115 can select the activity. For example, a particular activity may be selectable from an activities window and from a calendar window. The user in step 935 labels the fields with proper descriptions and may include a short label such as "Med", a medium label such as "Medication" and a long label such as "Medication Summary." Short, medium and long labels are described in greater detail above with reference to elements 664, 666 and 668 of FIG. 6C. The user in step 940 indicates the order in which the activities engine 425 will list the fields. The order field is described in greater detail with reference to tabOrder 646 of FIG. 6B. The user in step 945 selects the tables in which to store the data. Table location is described in greater detail with reference to location name 672 of FIG. 6C. The user in step 950 uses the information above to create the tables for storage in CM database 155. Step 950 may include using Tconfig 505 to generate an SQL file from input text to create the tables. Step 950 may further include using TcAll 515 to automate the use of Tconfig 505. Step 950 may still further include using CheckConfig 520 to check for errors in the configuration data 310. The user in step 955 then installs the clinical support data 315 so that the case manager 115 has a guideline to compare against the doctor's care plan. Method 900 then ends.

Figure 10:
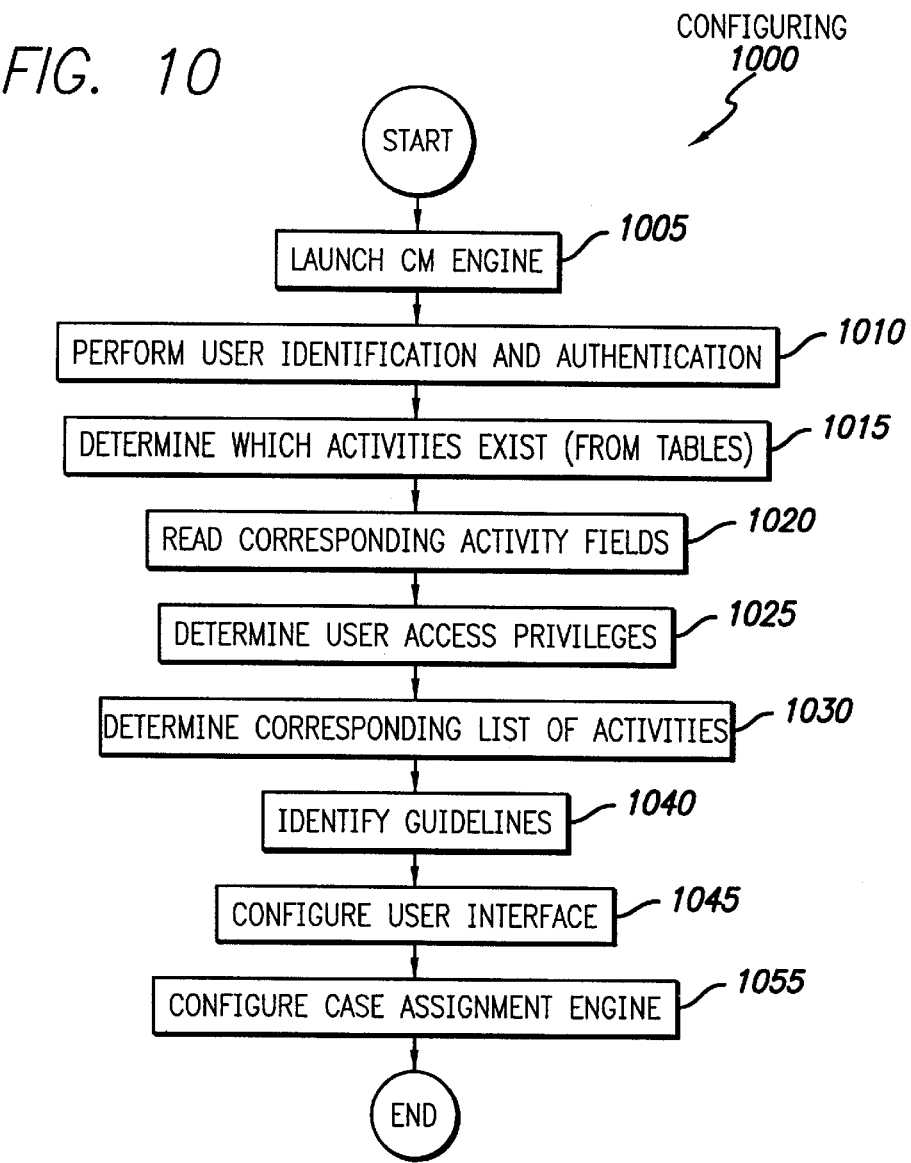
FIG. 10 is a flowchart illustrating a method for using the configuration tables to configure an application program.

FIG. 10 is a flowchart illustrating a method 1000 for configuring an application program in accordance with the present invention. Method 1000 begins with the case manager 115 in step 1005 launching the case manager client engine 293 (FIG. 2C). The security services in step 1010 performs user identification and authentication, for example, using a case manager identification number and a password. The activities engine 415 in step 1015 examine the activities template table 600 to determine which activities exist. For example, FIG. 6A illustrates that only two activities exist, namely, medication and disposition. The activities engine 415 in step 1020 reads the activity fields corresponding to each of the activities. To determine which activity fields relate to the activities, the activities engine 415 examines each of the column headers as a key field to determine whether another tables lists the activity fields. The security services 410 in step 1025 determine the security level of the authenticated case manager 115. The activities engine 415 in step 1030 determines whether the user has the appropriate privileges to view the activities and activity fields. To make an effective determination, the activities table and the activity fields table may include a column specifying the security level needed for the case manager 115 to view the activity or activity field. The search engine 430 in step 1040 retrieves any configuration data 310, such as the parameter variables available for the search engine 420 to apply. For example, the search engine 430 may be enabled to search the database 155 according to parameters entered into a query screen (see FIG. 8F1, FIG. 8F2 or FIG. 8F3). The list view engine 405 in step 1045 configures itself, i.e., the user interface portion, to display the proper client data 305, the proper columns of the patient menu 800, the proper columns of the patient record 820, etc. The activity engine 415 in step 1045 configures itself, e.g., the user interface, to display the appropriate fields and functions, e.g., the check-off button. The case assignment engine 440 in step 1055 retrieves configuration data 310 to determine the preferred method for assigning cases to the case managers 115. Method 1000 then ends.

Figure 11:
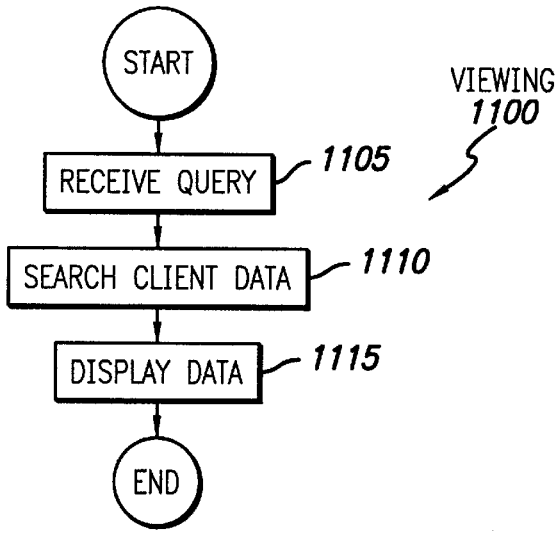
FIG. 11 is a flowchart illustrating a method for using the configuration tables to enable viewing data stored in the relational database.

FIG. 11 is a flowchart illustrating a method 1100 for viewing the patient data 305 in accordance with the present invention. Method 1100 begins with the search engine 430 in step 1105 receiving a search query. The search query may be obtained from an edit window, where the case manager 115 enters various search parameters. The search engine 430 may translate the text of the edit window to generate an SQL query for searching the case manager database 155. The search engine 430, in cooperation with the database server engine 250, in step 1110 searches the case manager database 155 including all common portions 710 and all extensions 705 and 715, according to the SQL query and generates search results. The list view engine 405 in step 1115 displays the search results of the search engine 430 according to the configuration data located in search results. For example, if the search parameters included "providers" with names starting with "br", then the list view engine 405 would present providers' names starting with "br" and including the columns defined in the list view columns of configuration data 310. Method 1100 then ends.

Figure 12:
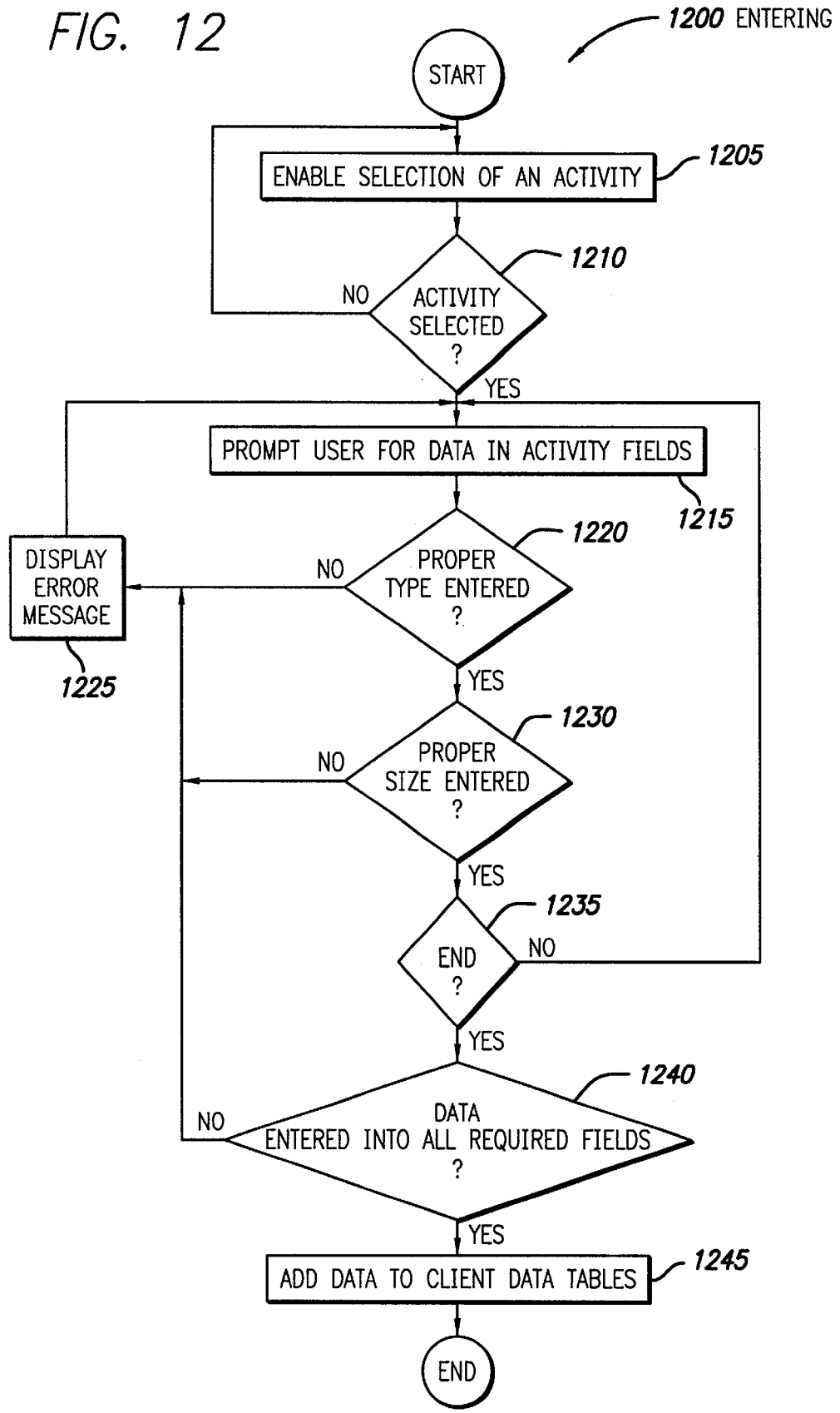
FIG. 12 is a flowchart illustrating a method for using the configuration tables to enable entering data into the relational database.

FIG. 12 is a flowchart illustrating a method 1200 for entering patient data 305 in accordance with the present invention. Method 1200 begins with the list view engine 405 in step 1205 enabling the selection of an activity. The list view engine 405 in step 1210 determines whether an activity is selected. If not, then method 1200 returns to step 1205. Otherwise, the activities engine 415 in step 1215 prompts the user for patient data 305 in the activity fields of a medications record edit window 882 (FIG. 8G).

The activities engine 415 in step 1220 determine whether the proper type of patient data 305 has been entered. If improper, then the activities engine 415 in step 1225 displays an error message and method 1200 returns to step 1215. Otherwise, method 1200 proceeds to step 1230. In step 1230, the activities engine 415 determines whether the proper size of patient data 305 has been entered. If improper, then the method 1200 returns to step 1225. Otherwise, method 1200 proceeds to step 1235. In step 1235, the activities engine 415 determines whether the user has indicated that the user intends to add no more data, such as by selecting an "OK" button 842. If the user has not indicated that no more data is to be entered, then method 1200 returns to step 1215. Otherwise, the activities engine 415 determines whether the data 305 has been entered into all the required fields. If not, then method 1200 returns to step 1225. Otherwise, method 1200 proceeds to step 1245. In step 1245, the activities engine 415 add the patient data 305 to the client data tables. Adding the data 305 to the tables may include dividing the data 305 into common and extension portions 705, 710 and 715 of the relational database 155. Method 1200 then ends.

The foregoing description of the preferred embodiments of the invention is by way of example only, and other variations of the above-described embodiments and methods are provided by the present invention. For example, the tables herein have been shown as separate tables; however, one skilled in the art will recognize that a single table can be used without departing from the spirit and scope of the present invention. Components of this invention may be implemented using a programmed general-purpose digital computer, using application specific integrated circuits, or using a network of interconnected conventional components and circuits. The embodiments described herein have been presented for purposes of illustration and are not intended to be exhaustive or limiting. The system is limited only by the following claims and equivalents thereof.

What is claimed is:

1. A method, comprising:
executing a software program having unconfigured behavior;
retrieving configuration data corresponding to the software program by the software program from a database having a database structure;
enabling dynamic configuration of a behavior of the software program by the software program in accordance with the configuration data without modifying the database structure;
obtaining non-configuration data by the configured software program; and
presenting the non-configuration data by the configured software program.

2. The method of claim 1, wherein the configuration data includes a set of items to be displayed.

3. The method of claim 2, wherein the configuration data includes a set of fields for each item.

4. The method of claim 1, wherein the configuration data includes font information.

5. The method of claim 1, wherein the configuration data includes user interface information.

6. The method of claim 1, wherein the configuration data includes order information.

7. The method of claim 1, wherein the configuration data includes version information.

8. The method of claim 1, wherein the configuration data includes preference information.

9. The method of claim 1, wherein the step of retrieving configuration data includes retrieving configuration data based on user information.

10. The method of claim 1, wherein the step of retrieving configuration data includes retrieving configuration data based on privilege information.

11. A system, comprising:
a software program having unconfigured behavior;
a database for storing configuration data corresponding to the software program, the database having a database structure; and
a processor, controlled by the software program, for enabling a behavior of the software program to be dynamically configured in accordance with the configuration data without modifying the database structure, the configured software program for obtaining, managing and presenting non-configuration data.

12. The system of claim 11, wherein the configuration data includes a table of items.

13. The system of claim 12, wherein the configuration data includes a table of fields.

14. The system of claim 11, wherein the configuration data includes font information.

15. The system of claim 11, wherein the configuration data includes user interface information.

16. The system of claim 11, wherein the configuration data includes order information.

17. The system of claim 11, wherein the configuration data includes version information.

18. The system of claim 11, wherein the configuration data includes preference information.

19. The system of claim 11, wherein the step of retrieving configuration data includes retrieving configuration data based on user information.

20. The system of claim 11, wherein the step of retrieving configuration data includes retrieving configuration data based on privilege information.

21. A system comprising:

means for executing a software program having unconfigured behavior;

software program means for retrieving configuration data corresponding to the software program means from a database, the database having a database structure; and processor means, controlled by the software program means, for enabling a behavior of the software program means to be dynamically configured in accordance with the configuration data without modifying the database structure, the configured software program means for obtaining, managing and presenting non-configuration data.

22. A computer-readable storage medium storing program code for causing a computer to perform the steps of:

executing a software program having unconfigured behavior;

retrieving configuration data corresponding to the software program by the software program from a database having a database structure;

enabling a behavior of the software program to be dynmaically configured by the software program in accordance with the configuration data and without modifying the database structure;

obtaining non-configuration data by the configured software program; and presenting the non-configuration data by the configured software program.

* * * * *